United States Patent
Wyslucha et al.

(10) Patent No.: US 10,072,793 B2
(45) Date of Patent: Sep. 11, 2018

(54) MEDICAL HOLDING ARM

(71) Applicant: MAQUET GMBH, Rastatt (DE)

(72) Inventors: Ulrich Wyslucha, Weingarten (DE); Stefan Peter, Rastatt (DE)

(73) Assignee: MAQUET GMBH, Rastatt (DE)

( * ) Notice: Subject to any disclaimer, the term of this patent is extended or adjusted under 35 U.S.C. 154(b) by 367 days.

(21) Appl. No.: 14/648,865

(22) PCT Filed: Dec. 3, 2013

(86) PCT No.: PCT/EP2013/075337
§ 371 (c)(1),
(2) Date: Jun. 1, 2015

(87) PCT Pub. No.: WO2014/095338
PCT Pub. Date: Jun. 26, 2014

(65) Prior Publication Data
US 2015/0297305 A1   Oct. 22, 2015

(30) Foreign Application Priority Data
Dec. 20, 2012   (DE) .......................... 10 2012 112 716

(51) Int. Cl.
*F16B 7/02* (2006.01)
*F16C 11/10* (2006.01)
(Continued)

(52) U.S. Cl.
CPC ........... *F16M 13/022* (2013.01); *A61B 90/50* (2016.02); *F16B 7/02* (2013.01); *F16C 11/10* (2013.01);
(Continued)

(58) Field of Classification Search
CPC ..... A61B 90/50; A61B 2090/508; F16B 7/02; F16C 11/10; F16D 1/0876; F16D 1/12;
(Continued)

(56) References Cited

U.S. PATENT DOCUMENTS 3,379,034 A * 4/1968 Gustafson ............... F16D 7/046
139/449
3,419,295 A   12/1968 Small
(Continued)

FOREIGN PATENT DOCUMENTS

CN   101849132 A   9/2010
CN   102462533 A   5/2012
(Continued)

OTHER PUBLICATIONS

Translation of DE 102 09 209. Hartwig, Helmut. Continuous locking system for sections of robot arm comprises ring of locking bolts on one section and different number of bores in ring on other, at least two bolts engaging with bores in all positions of sections. Feb. 19, 2004.*
(Continued)

*Primary Examiner* — Josh Skroupa

(57) ABSTRACT

A medical holding arm, comprising at least one joint with two joint bodies which are rotatable relative to each other about a rotational axis (D), wherein a first of the joint bodies has a plurality of locking pins and a second of the joint bodies has a plurality of locking recesses, the number of locking pins differs from the number of locking recesses, the locking pins each have an axially tapered engagement part, the locking recesses are respectively formed axially tapered to selectively receive each of the engagement parts for locking the joint, and when the joint is locked, at least one of the locking pins is received with its tapered engagement part completely in one of the tapered locking recesses, while at least one of the other locking pins is received with its tapered engagement part only partially in one of the other tapered locking recesses.

20 Claims, 4 Drawing Sheets

(51) Int. Cl.
  *F16M 11/06* (2006.01)
  *F16M 13/02* (2006.01)
  *F16D 1/12* (2006.01)
  *A61B 90/50* (2016.01)

(52) U.S. Cl.
  CPC .............. *F16D 1/12* (2013.01); *F16M 11/06* (2013.01); *A61B 2090/508* (2016.02); *Y10T 403/125* (2015.01); *Y10T 403/32418* (2015.01); *Y10T 403/32581* (2015.01); *Y10T 403/64* (2015.01)

(58) Field of Classification Search
  CPC ........ F16M 11/06; F16M 11/08; F16M 11/10; F16M 13/022
  USPC ............. 403/4, 84, 103, 104, 116, 306, 321, 403/322.1, 335, 409.1; 464/38, 44
  See application file for complete search history.

(56) References Cited

U.S. PATENT DOCUMENTS

| | | | |
|---|---|---|---|
| 3,803,667 | A | 4/1974 | Rose |
| 4,971,037 | A | 11/1990 | Pelta |
| 6,283,912 | B1 | 9/2001 | Hu et al. |
| 6,767,153 | B1 | 7/2004 | Holbrook |
| 8,216,211 | B2 | 7/2012 | Mathis |
| 2002/0026190 | A1 | 2/2002 | Walulik et al. |
| 2004/0143153 | A1 | 7/2004 | Sharrow |
| 2006/0058579 | A1 | 3/2006 | Oberlaender et al. |
| 2006/0074406 | A1 | 4/2006 | Cooper et al. |
| 2006/0234798 | A1* | 10/2006 | Chang ................... F16D 7/046 464/38 |
| 2008/0086150 | A1 | 4/2008 | Mathis |
| 2009/0036890 | A1 | 2/2009 | Karidis |
| 2010/0298648 | A1 | 11/2010 | Gray |

FOREIGN PATENT DOCUMENTS

| | | | | |
|---|---|---|---|---|
| DE | 2055681 | B | * 7/1976 | ............ F16D 27/14 |
| DE | 3509879 | A1 | * 9/1985 | ............ A61F 2/582 |
| DE | 10209209 | A1 | 2/2004 | |
| DE | 102009009575 | A1 | 8/2010 | |
| EP | 1826301 | A1 | 8/2007 | |
| EP | 0862385 | B1 | 12/2007 | |
| EP | 1357829 | B1 | 10/2010 | |
| JP | 2001-517101 | A | 10/2001 | |
| JP | 3519328 | B2 | 4/2004 | |
| JP | 2006187815 | A | 7/2006 | |
| JP | 2009-174673 | A | 8/2009 | |
| JP | 3166092 | U | 2/2011 | |
| WO | 03017853 | A1 | 3/2003 | |

OTHER PUBLICATIONS

Japanese Office Action dated May 10, 2016 which issued during the prosecution of corresponding Japanese Patent Application No. 2015-541195, 5 pages (with English translation, 4 pages).

Translated search report for the first Office Action for CN201380055793.0, which corresponds to this application, dated Jul. 1, 2016, 2 pages.

Translated search report for the first Office Action for CN201380056361.1, which corresponds to this application, dated Jul. 29, 2016, 2 pages.

International Search Report for PCT/EP2013/075337 dated Apr. 15, 2014.

* cited by examiner

MEDICAL HOLDING ARM

CROSS REFERENCE TO RELATED APPLICATIONS

This application is entitled to the benefit of and incorporates by reference subject matter disclosed in International Patent Application No. PCT/EP2013/075337 filed on Dec. 3, 2013, and German Application No. 10 2012 112 716.6 filed on Dec. 20, 2012.

TECHNICAL FIELD

The invention relates to a medical holding arm.

BACKGROUND

Nowadays, for surgical applications increasingly assistance systems are used, comprising a holding arm, which is for example attachable to the slide rail of an operating table. For example, such a holding arm is used in shoulder operations for supporting the arm. It includes a plurality of rigid holding members which are movably coupled to each other by joints. Thus, the holding arm may be moved freely in all spatial directions and be fixed securely in the desired position.

The joints, which couple respectively two rigid holding members of the holding arm freely movable to each other, include a first joint body connected to one of the holding members and a second joint body connected to the other holding member. In order to fix the holding members in a desired arrangement with respect to each other, the two joint bodies have to be locked relative to each other.

A possibility for such a locking is described in DE 102 09 209 B4. Therein, one of the joint bodies includes a plurality of locking pins, while corresponding locking recesses are formed at the other joint body. An essential feature of said locking mechanism is that the number of locking recesses is higher than the number of locking pins. In a specific embodiment, thirteen locking recesses and twelve locking pins are provided. In the locked state, respectively one of the locking pins engages completely in one of the locking recesses, while the locking pins immediately adjacent to said pin are only partially inserted in their associated locking recesses. Thus, the clearance-free locking of the joint is assisted.

In order to allow this kind of engaging of the locking pins in the locking recesses, the locking pins respectively include an engagement part having the shape of a truncated cone. The locking recesses are correspondingly tapered in a truncated cone-shaped manner. This ensures that in the locked state of the joint, said locking pin being completely inserted in the corresponding locking recess contacts the locking recess with its engagement part over the entire surface. In contrast, the engagement parts of said locking pins being only partially inserted in the corresponding locking recesses only have line contact or only a very slight surface contact with the corresponding locking recesses.

In practical use, it turned out that a holding arm using a locking of the above-explained type is subject to certain restrictions with respect to high load applications. Thus, the holding arm has to be operated by means of a handle, which is coupled to an unlocking mechanism acting on the joints, in order to unlock the joints. The higher the load, the more manual force has to be exerted.

SUMMARY

It is the object of the invention to amend a holding arm of the above-described type such that higher load applications can conveniently be handled by the user.

The invention solves this object by a holding arm wherein a first of the joint bodies has a plurality of locking pins and a second of the joint bodies has a plurality of locking recesses, the number of locking pins differs from the number of locking recesses, the locking pins each have an axially tapered engagement part, the locking recesses are respectively formed axially tapered to selectively receive each of the engagement parts for locking the joint, and, when the joint is locked, at least one of the locking pins is received with its tapered engagement part completely in one of the tapered locking recesses, while at least one of the other locking pins is received with its tapered engagement part only partially in one of the other tapered locking recesses, wherein the engagement part of the respective locking pin has at least one first flattened contact surface, and the respective locking recess has at least one second flattened contact surface, and, when the engagement part of the respective locking pin is received in the respective locking recess, the first and the second contact surface are at least partially in flat contact with each other.

According to the invention, the engagement part of the respective locking pin hast at least one first flattened contact surface. Correspondingly, also the respective locking recess has at least one second flattened contact surface. When the engagement part of the locking pin is received in the locking recess, the first and the second contact surface have at least partially a flat contact to each other.

Flattening of the first or the second contact surface according to the invention means that the respective contact surface is at least not as much curved than the remaining, preferably conical, surface of the engagement part of the locking pin or the locking recess. Thus, a flat contact between locking pin and locking recess in the region of the two contact surfaces is ensured, in particular also when the engagement part of the respective locking pin is inserted only partially in the corresponding locking recess. Thus, higher load applications are possible than by means of the locking mechanism described in DE 102 09 209 B4, which allows only for an approximately line-shaped contact between locking pin and locking recess due to the truncated cone-shaped design of the locking pin and the locking recess in case of a not complete engagement.

Thus, due to the shaping according to the invention it is achieved that the components being engaged, namely the engagement part of the locking pin and the locking recess always, i.e. in particular also in case of low insertion depth, contact each other in a flat manner causing the surface pressure between said components to be reduced. Due to the low break-off torque caused by the low elastic deformation and the lack of cold welding effects, the locked joint can be released with substantially lower manual force than previously.

This has a particularly positive effect, when the locking pin only partially engages the locking recess. Further, this results in a higher wear resistance at the edges of the respective locking pin.

Due to the higher load capacity, the holding arm according to the invention may be used for other applications than previously, in particular in highly loaded and dynamic areas of application, e.g. leg applications, body supports and the like. The holding arm is now also insensitive with respect to impulse loadings occurring for example when driving in artificial limbs.

Preferably, the first and the second contact surface are formed respectively from a flat surface. Such flat contact surfaces particularly reliably provide the desired flat contact of a locking pin not completely engaging the corresponding locking recess, in order to reduce the surface pressure in this manner. However, it is to be pointed out that the contact surfaces do not have to be formed completely flat, in order to reduce the surface pressure. Also slightly curved contact surfaces may be used, if they are suited for providing the desired flat contact.

In a particularly preferred embodiment, the respective locking recess is formed as truncated pyramid, wherein the second contact surface is formed from a side surface of the locking recess formed in this manner. For example, the truncated pyramid has a rectangular base area. However, this design is only intended as an example. Thus, the respective locking recess can also have another shape, e.g. the shape of an oblong hole with two opposite parallel side surfaces and two opposite obliquely tapered side surfaces.

In a particularly preferred embodiment, the truncated pyramid is dimensioned so large that the engagement part of the respective locking pin, when being completely engaged, only contacts the locking recess in the region of its contact surface. Thus, any line contact between locking pin and locking recess, causing a negatively high surface pressure, is prevented.

Preferably, the at least one first contact surface of the respective locking pin includes at least two contact surfaces, which are arranged on diametrically opposed sides of the engagement part of the locking pin. In this case, also the respective locking recess preferably has two diametrically arranged second contact surfaces. Thus, depending on the rotational position of the two joint plates, one of the two first contact surfaces always contacts one of the two second contact surfaces.

Preferably, the respective locking pin with its engagement part received in the respective locking recess only contacts the locking recess in the region of the contact surface thereof specifically provided for this purpose, namely the second contact surface of said locking recess. This prevention of a contact between locking pin and locking recess outside of the two contact surfaces in turn prevents any undesired line contact between locking pin and locking recess and renders the joint insensitive with respect to manufacturing tolerances, joint play and elastic position changes under load.

In a preferred embodiment, the locking pins and the locking recesses respectively form a circular arrangement. Preferably, the first contact surfaces of the locking pins and the second contact surfaces of the locking recesses are respectively aligned along said circular arrangement. This means that both the first contact surfaces and the second contact surfaces are respectively penetrated by an imaginary circular line along which the locking pins or the locking recesses are arranged.

Further advantageous embodiments of the invention are included in the dependent claims as well as the following description.

BRIEF DESCRIPTION OF THE DRAWINGS

The invention will be described in more detail on the basis of the Figures, wherein.

DETAILED DESCRIPTION

Figure 1:
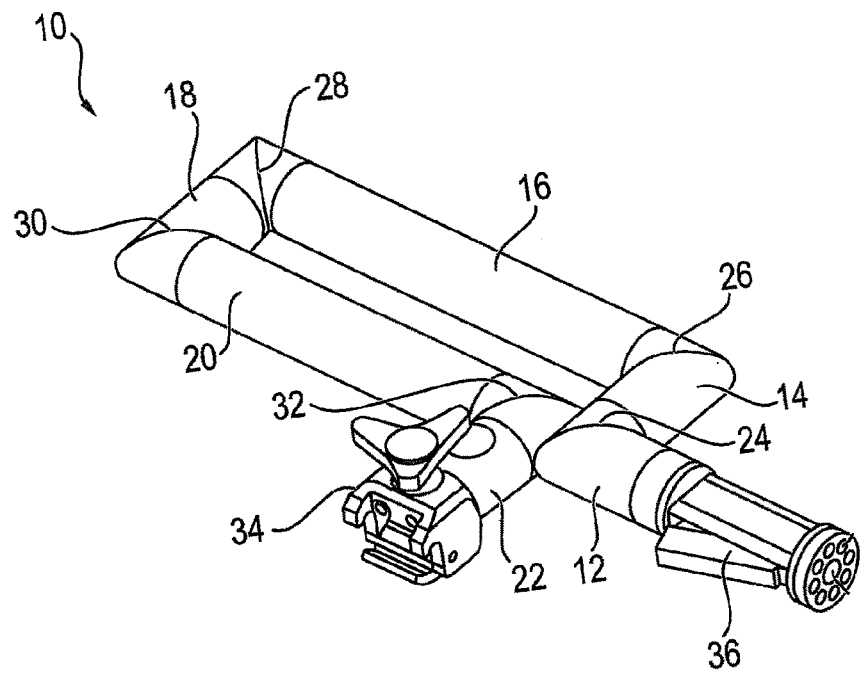
FIG. 1 shows a holding arm according to the invention.

FIG. 1 shows a holding arm 10 which includes a plurality of rigid holding members 12, 14, 16, 18, 20 and 22 being coupled to each other by joints 24, 26, 28, 30 and 32. At one end of the holding arm 10 a mounting device 34 is arranged serving to attach the holding arm 10 to a slide rail (not shown) of an operating table. At the other end of the holding arm 10 a handle 36 is positioned, which can be manually operated by the user in order to unlock the holding arm 10.

If no operating force is exerted on the handle 36, the holding members 12, 14, 16, 18, 20 and 22 of the holding arm 10 are rigidly coupled to each other by the joints 24, 26, 28, 30 and 32. In this state, the holding arm 10 forms a rigid unit.

If the user presses the handle 36, the holding members 12, 14, 16, 18, 20 and 22, coupled to each other by the joints 24, 26, 28, 30 and 32, become movable relative to each other via an unlocking mechanism, so that the user can orient the holding arm 10 in space as desired. If the user subsequently releases the handle 36 again, the joints 24, 26, 28, 30 and 32 are locked and the holding arm 10 is fixed in its changed orientation.

Below, the construction and operating mode of one of the identically constructed joints 24, 26, 28, 30 and 32 is explained on the basis of FIGS. 2 to 8. It is exemplarily referred to the joint 24.

Figure 2:
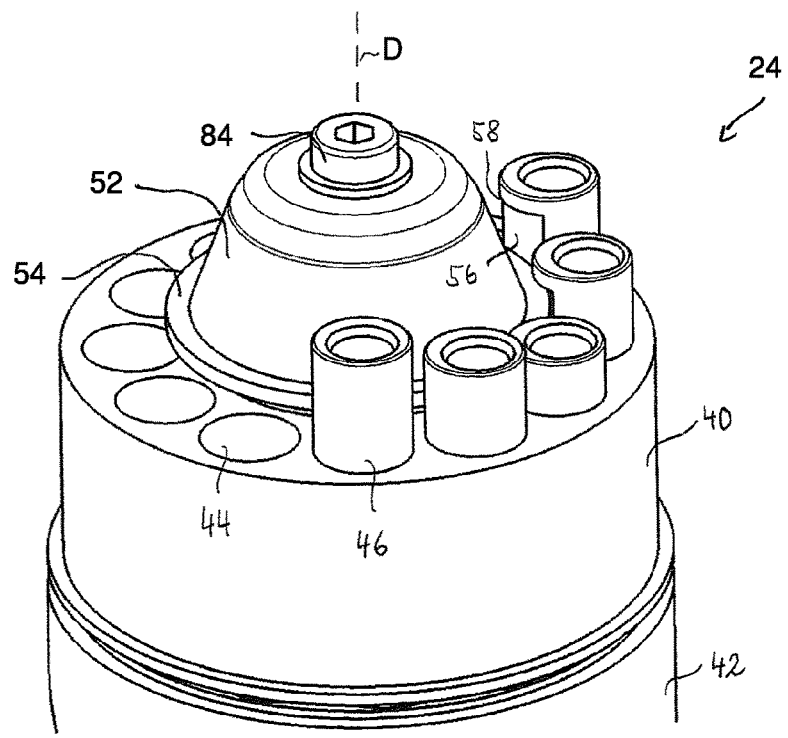
FIG. 2 shows a joint of the holding arm according to FIG. 1.

As shown in FIG. 2, the joint 24 includes a first joint body 40 in the shape of a revolver and a second joint body 42 in the shape of a joint plate. The first joint body 40 is coupled to the first holding member 12 and the second joint body 42 is coupled to the holding member 14. In the locked state of the joint 24, the two joint bodies 40 and 42 are rigidly coupled to each other, while, in the unlocked state of the joint 24, they are rotatable relative each other about a rotational axis D being coincident with the center axes of the two joint bodies 40 and 42.

The revolver 40 has a plurality of through-bores 44, preferably arranged in a circular manner, in which locking pins 46 are axially guided. In the present embodiment, twelve through-bores 44 and correspondingly twelve locking pins 46 are provided, wherein only five of the twelve locking pins 46 are illustrated in FIGS. 2 to 5.

Figure 3:
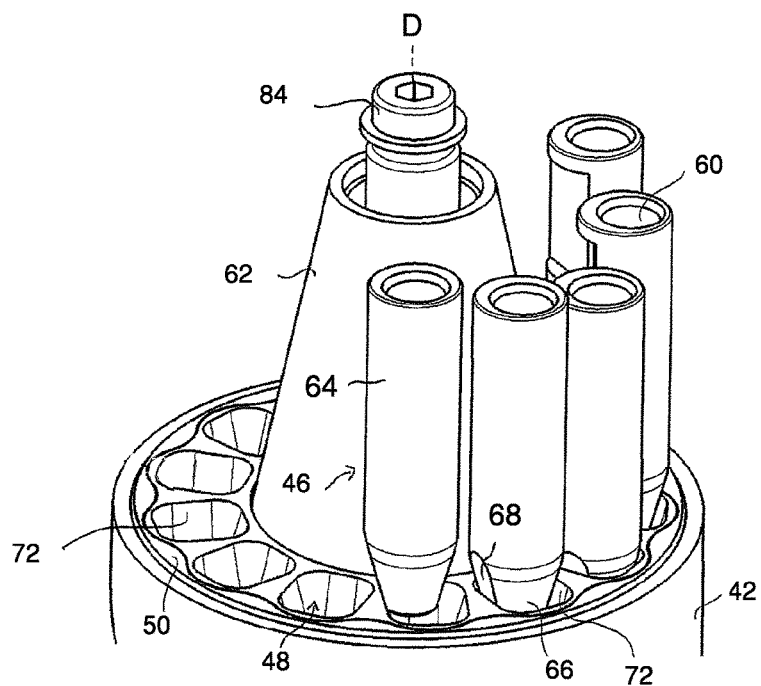
FIG. 3 shows the joint according to FIG. 2, wherein one of the joint bodies was omitted.

As shown in the illustration according to FIG. 3, in which the first joint body 40 is omitted, the second joint body 42 includes a plurality of locking recesses 48. The locking recesses 48 are formed in a locking disc 50, which is inserted in the second joint body 42. The locking recesses 48 serve for receiving the locking pins 46, in order to lock the two joint bodies 40 and 42 in the manner described below. It should be noted here that the number of locking recesses 48 differs from the number of locking pins 46. In the present embodiment, in which twelve locking pins 46 are provided, the second joint body 42 includes thirteen locking recesses 48.

As shown in FIG. 2, on the top surface of the first joint body 40 a bell-shaped lever-element 52 is mounted, which serves for unlocking the joint 24. For this, the lever element 52 cooperates with unlocking rods (not shown in the Figures) which are operable by means of the handle 36, in order to move the lever element 52 along the rotational axis D (in FIG. 2 above). The lever element 52 includes an annular flange 54 at its lower edge. The locking pins 46 respectively have a recess 56 facing the annular flange 54, in which recess 56 the annular flange 54 engages. Due to the recess 56 a step 58 is formed at the respective locking pin 46, with which the annular flange 54 (in FIG. 2 from below) abuts, when the lever element 52 is raised by means of the unlocking rods along the rotational axis D. If the lever element 52 is raised far enough, it carries the locking pins 46 along so far via its annular flange 54 that said locking pins 46 are released from the locking recesses 48. In this state, the two joint bodies 40 and 42 are rotatable relative to each other about the rotational axis D.

The locking pins 46 are resiliently supported in their associated through-bores 44 of the first joint body 40. For this, a biasing element (not shown in the Figures) is associated to each locking pin 46, wherein the biasing element is arranged in a receiving bore 60 formed in the locking pin 46 (cf. FIGS. 4 and 6). A vent bore 61 is adjacent to the receiving bore 60.

Due to the biasing elements the locking pins 46 are biased against the second joint body 42. If one of the locking pins 46 is positioned in the area of one of the locking recesses 44, it is thus pressed entirely or partially into the locking recess 44. Thus, the lever element 42 releases the locking pins 46 against this biasing force from the locking recesses 44.

The first joint body 40 is supported on a bearing cone 62 shown in FIG. 3. The lever element 42 is mounted on push rods (not shown) by means of a fixing screw 84. The lever element 52 is arranged above the bearing cone 62.

As mentioned above, the number of locking pins 46 differs from the number of locking recesses 44. Thus, the angular distance of two immediately adjacent locking pins 46 differs from the angular distance of two immediately adjacent locking recesses 48. This results in a nonius-like association of the locking pins 46 to the locking recesses 48. Because of this nonius-like association, in the present embodiment in the locked state of the joint 24, respectively only one of the locking pins 46 is completely inserted in one of the locking recesses 48, while the locking pins 46 adjacent to said completely inserted locking pin are successively less deeply received in the locking recesses 48 associated to them. In contrast, the remaining locking pins 46 are arranged on the top surface of the locking disc 50, without being inserted in one of the locking recesses 48. This nonius-like association between the locking pins 46 and the locking recesses 48 can in particular also be seen in the developed view according to FIG. 4 and the partially sectional view according to FIG. 6.

The locking pins 46 respectively have a pin body 64 and an axially tapered engagement part 66 adjacent thereto. In the present embodiment, the engagement part 66 is substantially formed as truncated cone. According to the invention, on diametrically opposed sides of said truncated cone-shaped engagement part 66 two flattened, preferably flat contact surfaces 68 are formed, which respectively extend over the entire length of the engagement part 66. In the perspective illustration according to FIG. 3, respectively only one of said two contact surfaces 68 is shown, while in the sectional illustration according to FIG. 5 respectively both contact surfaces 68 are indicated.

In the present embodiment, the locking recesses 48 respectively have the shape of a truncated pyramid, which has an approximately rectangular base area. Due to this truncated pyramid design the respective locking recess 48 has two side surfaces 72, which are associated to the two contact surfaces 68 of the corresponding locking pin 46 and contact them, when the locking pin 46 is inserted in the locking recess 48. Thus, the two above-mentioned side surfaces 72 of the locking recess 48 form contact surfaces which are intended to contact the contact surfaces 68 of the locking pin 46.

Figure 4:
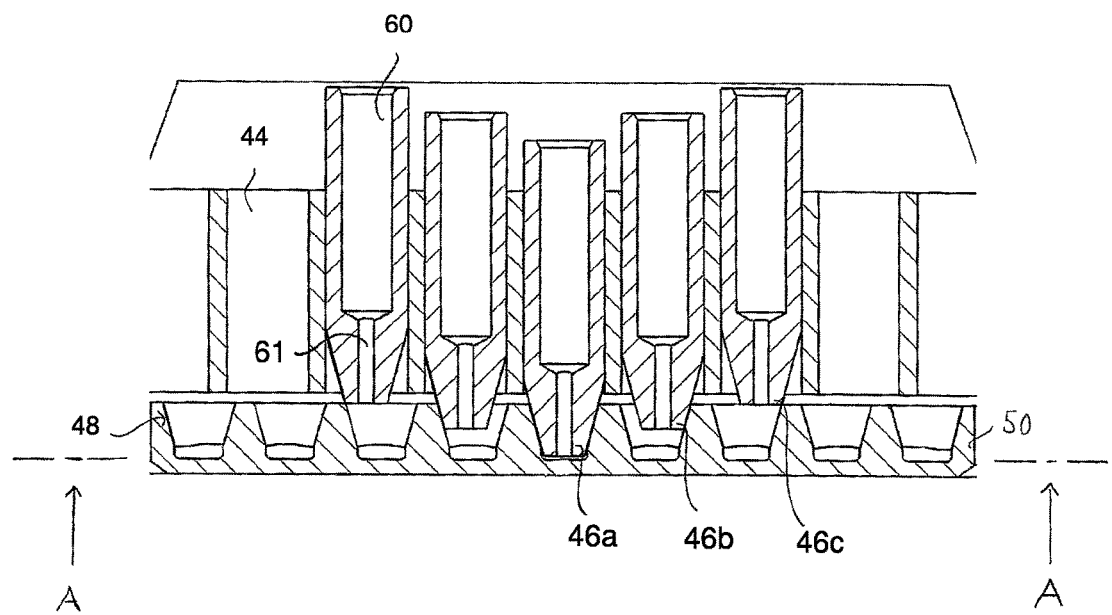
FIG. 4 shows a developed cross-sectional view of the joint.
Figure 5:
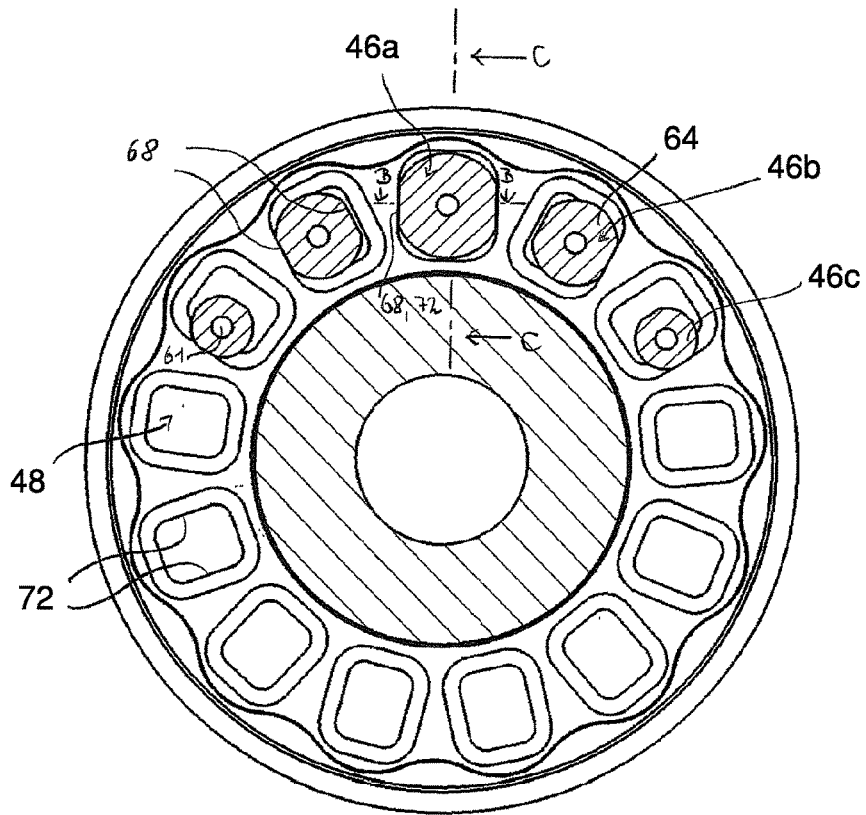
FIG. 5 shows the section A-A according to FIG. 4 as sectional top view.
Figure 6:
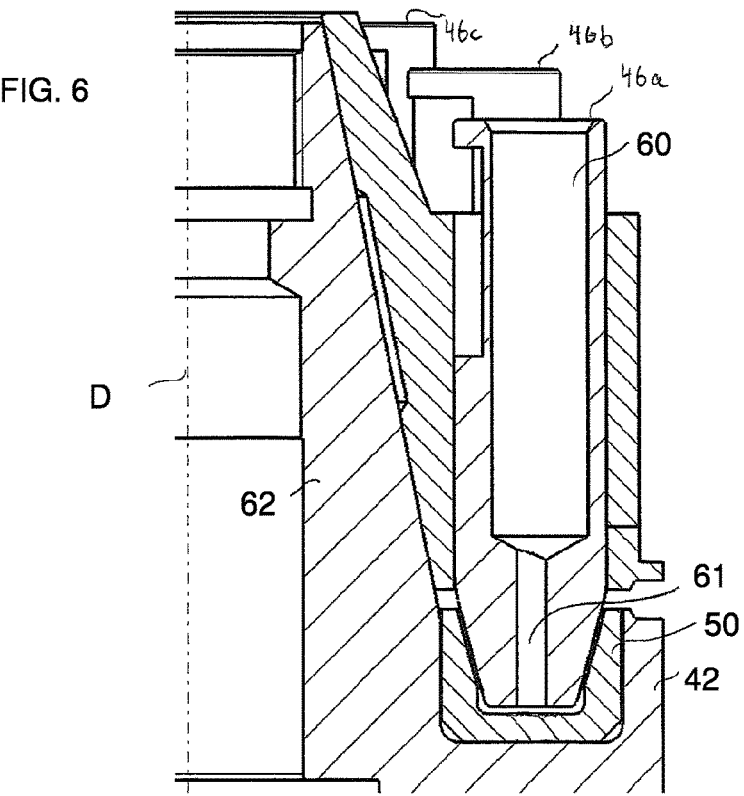
FIG. 6 shows a further sectional view with a locking pin received in a locking recess.

Particularly FIGS. 4 and 5 illustrate how the locking pins 46 contact the locking recesses 48 in a flat manner depending on their insertion depth according to the invention. In these Figures, said locking pin inserted completely in the corresponding locking recess is designated 46a, while the two locking pins immediately adjacent thereto being respectively only partially inserted in the corresponding locking recesses are designated 46b. The locking pins designated 46c in FIGS. 4 and 5, are only marginally inserted in the corresponding locking recesses.

Figure 7:
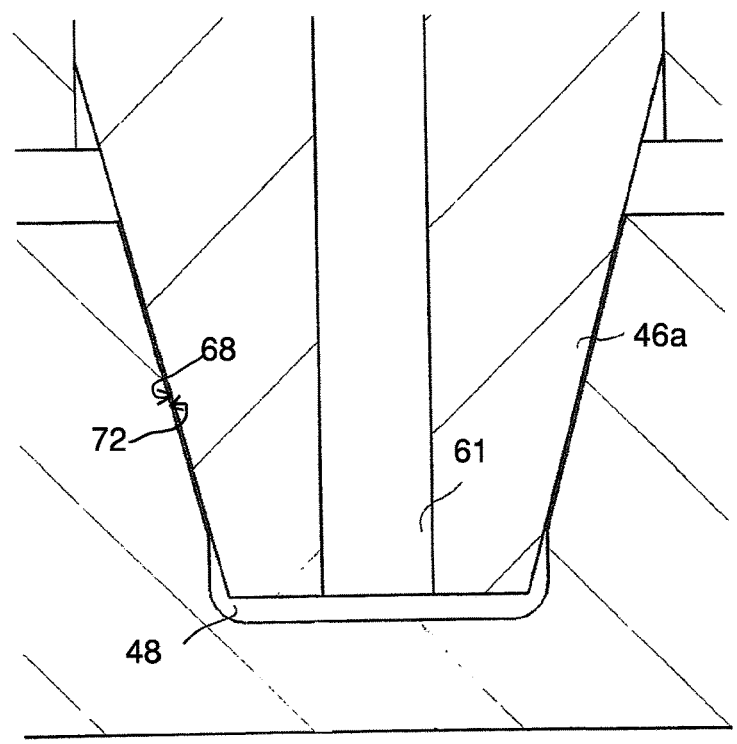
FIG. 7 shows the section B-B according to FIG. 5.
Figure 8:
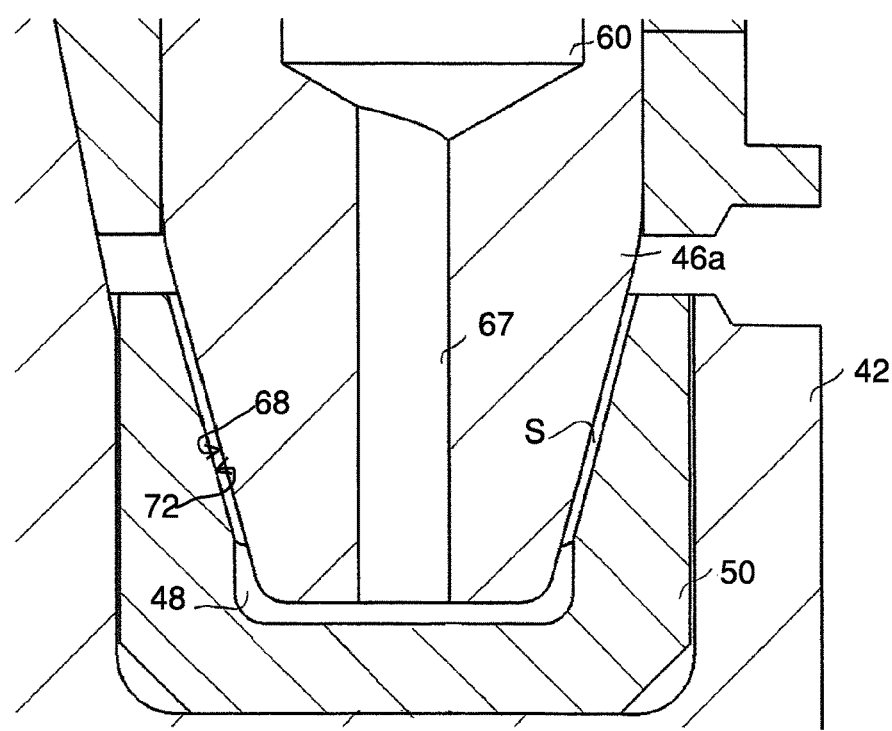
FIG. 8 shows the section C-C according to FIG. 5.

As shown in FIG. 5, the completely inserted locking pin 46a abuts with its two contact surfaces 68 fully on the two contact surfaces 72 of the corresponding locking recess 48. It should be noted here that the locking pin 46a only contacts the locking recess 48 with its two contact surfaces 68, i.e. has a clearance with respect to the side walls of the locking recess 48 outside of these contact surfaces 68. This feature is again illustrated in the illustrations according to FIG. 7 and FIG. 8. FIG. 7 shows the section B-B, and FIG. 8 shows the section C-C according to FIG. 5. The clearance between the locking pin 46a and the locking recess 48 is designated S in FIGS. 7 and 8. FIGS. 7 and 8 also show that the front surface of the completely inserted locking pin 46a has a small distance from the bottom of the locking recess 48 in order to prevent being placed on the bottom. In order to guarantee a certain manufacturing tolerance with respect thereto, the locking recess 48 is not axially tapered anymore near its bottom.

The locking pins 46b, which are only partially inserted and immediately adjacent to the completely inserted locking pin 46a, only contact the corresponding contact surface 72 of the respective locking recess 46 with one of their contact surfaces 68. Apart from that flat contact they do not contact the side walls of their associated recesses 48 as well. The same applies to the locking pins 46c, which are only very slightly inserted in the corresponding locking recesses 48.

As shown in FIG. 5, the flat contact surfaces 68 of the locking pins 46 and the flat contact surfaces 72 of the locking recesses 48 are arranged such that they are aligned along an imaginary circle, which defines the circular arrangement of the locking pins 46 and the locking recesses 48. Along said circle the locking pins 46 and the locking recesses 48 are rotated relative to each other, when the two joint bodies 40 and 42 are moved relative to each other. Thus, the surface pressure between the contact surfaces 68 and 72 acts in the direction of the rotational movement of the two joint bodies 40 and 42.

As can in particular be seen in the illustration according to FIG. 5, by providing the flattened contact surfaces 68 and 72 according to the invention it is ensured that the locking pins 46 have a flat contact with the corresponding locking recess 48 for each insertion depth. In particular, if the locking pins 46 are not completely inserted, the line contact occurring in prior art is prevented and the surface pressure is reduced.

As the completely inserted locking pin 46a only contacts the locking recess 48 in the region of its contact surfaces 68, a jamming of the locking pin 46a is prevented. This also applies to the only partially inserted locking pins 46b and 46c. Thus, also overdeterminations, tolerance variations and axis errors can be avoided.

Although various embodiments of the present invention have been described and shown, the invention is not restricted thereto, but may also be embodied in other ways within the scope of the subject-matter defined in the following claims.

What is claimed is:

1. A medical holding arm, comprising at least one joint disposed at the junction of a pair of joint bodies, the pair of joint bodies comprising a first and second joint body, the first and second joint bodies are rotatable relative to each other about a rotational axis, wherein:
   the first joint body comprises a plurality of locking pins configured to mechanically engage a plurality of recesses of the second joint body,
   at the at least one joint, the number of locking pins of the first joint body differs from the number of locking recesses of the second joint body, and at the at least one joint the locking pins each have an axially tapered engagement part and
   the locking recesses are axially tapered to selectively receive at least a portion of the engagement parts for locking the joint, and,
   wherein when the at least one joint is locked, at least one of the locking pins of the plurality of locking pins is received with its tapered engagement part completely in one of the tapered locking recesses of the plurality of recesses, while at least one of the other locking pins of the plurality of locking pins is received with its tapered engagement part only partially in one of the other tapered locking recesses of the plurality of locking recesses, wherein
   the engagement part of the plurality of locking pins has at least one first flattened contact surface, and the locking recess of the plurality of locking recesses has at least one first flattened contact surface such that when the engagement part of the at least one locking pin is received in the locking recess of the one of the tapered locking recesses, the first contact surfaces of the locking pin and locking recess establish at least partial flat contact with each other.

2. The holding arm according to claim 1, wherein the first contact surface of the locking pin and the first contact surface of the locking recess are formed as flat surfaces.

3. The holding arm according to claim 2, wherein that the engagement part of the locking pin is formed as a truncated cone on which the first contact surface is formed.

4. The holding arm according to claim 2, wherein the locking recess is formed as a truncated pyramid and the second contact surface is formed from a side surface of the locking recess formed in this manner.

5. The holding arm according to claim 2, wherein the at least one first contact surface of the locking pin comprises at least two contact surfaces, and the at least two contact surfaces are arranged on diametrically opposed sides of the engagement part of the locking pin.

6. The holding arm according to claim 2, wherein the locking pin, when its respective engagement part is received in the locking recess, only contacts the locking recess with its first contact surface.

7. The holding arm according to claim 1, wherein the engagement part of the first of the tapered locking pins is formed as a truncated cone on which the first contact surface is formed.

8. The holding arm according to claim 7, wherein the locking recess is formed as a truncated pyramid and the second contact surface is formed from a side surface of the locking recess formed in this manner.

9. The holding arm according to claim 7, wherein the at least one first contact surface of the locking pin comprises at least two contact surfaces, and the at least two contact surfaces are arranged on diametrically opposed sides of the engagement part of the locking pin.

10. The holding arm according to claim 7, wherein the locking pin, contacts the locking recess with its first contact surface of its engagement part when the locking pin is received in the locking recess.

11. The holding arm according to claim 1, wherein the locking recess of the first of the plurality of tapered locking recesses is formed as a truncated pyramid and the second contact surface is formed from a side surface of the first of the plurality of tapered locking recesses.

12. The holding arm according to claim 11, wherein the at least one first contact surface of the locking pin comprises at least two contact surfaces, and the at least two contact surfaces are arranged on diametrically opposed sides of the engagement part of the locking pin.

13. The holding arm according to claim 1, wherein the at least one first contact surface of the first of the tapered locking pins comprises at least two contact surfaces, the at least two contact surfaces are arranged on diametrically opposed sides of the engagement part of the first of the tapered locking pins.

14. The holding arm according to claim 1, wherein the first of the tapered locking pins, when its engagement part is received in the locking recess of the first of the plurality of tapered locking recesses, only contacts the locking recess of the first of the plurality of tapered locking recesses with its first contact surface.

15. The holding arm according to claim 1, wherein the plurality of tapered locking pins and the plurality of tapered locking recesses each form a circular arrangement.

16. The holding arm according to claim 15, wherein the first contact surfaces of the plurality of tapered locking pins and the first contact surfaces of the plurality of tapered locking recesses are aligned along the circular arrangement.

17. The holding arm according to claim 1, wherein the first joint body has a plurality of through-bores, in which at least one of the locking pins is axially guided.

18. The holding arm according to claim 1, wherein the plurality of tapered locking pins are resiliently supported at the first joint body and biased against the second joint body.

19. The holding arm according to claim 1, wherein the number of locking recesses is of a greater magnitude than the number of locking pins.

20. The holding arm according to claim 1, further comprising at least two rigid holding members, wherein a first holding member of said at least two rigid holding members is coupled to the first joint body and the second holding member of said at least two rigid holding members is coupled to the second joint body.

* * * * *